United States Patent
Segal et al.

(10) Patent No.: US 7,137,654 B2
(45) Date of Patent: *Nov. 21, 2006

(54) FASTENING MECHANISM FOR MEDICAL CONNECTORS

(75) Inventors: Scott Segal, Walpole, MA (US); Stephen B. Corn, Sharon, MA (US)

(73) Assignee: QD Enterprises LLC, Sharon, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/191,604

(22) Filed: Jul. 27, 2005

(65) Prior Publication Data

US 2006/0087120 A1   Apr. 27, 2006

Related U.S. Application Data

(63) Continuation of application No. 10/650,093, filed on Aug. 26, 2003, now abandoned, which is a continuation of application No. 10/124,288, filed on Apr. 17, 2002, now Pat. No. 6,612,624, which is a continuation-in-part of application No. 09/094,433, filed on Jun. 8, 1998, now Pat. No. 6,402,207.

(51) Int. Cl.
*F16L 25/00*   (2006.01)

(52) U.S. Cl. ............... 285/330; 285/360; 285/376; 285/401; 285/914

(58) Field of Classification Search ............... 285/330, 285/360, 361, 376, 396, 401, 402, 913, 914
See application file for complete search history.

(56) References Cited

U.S. PATENT DOCUMENTS

| | | | | |
|---|---|---|---|---|
| 3,170,667 A | * | 2/1965 | Szohatzky | ............... 251/149.6 |
| 3,287,031 A | * | 11/1966 | Simmons et al. | ............. 285/27 |
| 4,080,737 A | * | 3/1978 | Fleer | ......................... 433/126 |
| 4,116,476 A | * | 9/1978 | Porter et al. | ............. 285/124.4 |
| 4,150,673 A | * | 4/1979 | Watt | ........................... 604/408 |
| 4,211,439 A | * | 7/1980 | Moldestad | ..................... 285/27 |
| 4,280,723 A | * | 7/1981 | Moldestad | ................... 285/376 |
| 4,619,640 A | * | 10/1986 | Potolsky et al. | ............... 604/7 |
| 4,682,981 A | * | 7/1987 | Suzuki et al. | ............... 604/158 |
| 4,790,567 A | * | 12/1988 | Kawano et al. | ................ 285/24 |
| 5,405,339 A | * | 4/1995 | Kohnen et al. | ............. 604/535 |
| 5,562,121 A | * | 10/1996 | Hodges et al. | ............. 137/360 |
| 5,616,133 A | * | 4/1997 | Cardenas | ..................... 604/187 |
| 5,620,427 A | * | 4/1997 | Werschmidt et al. | ....... 604/535 |
| 5,632,735 A | * | 5/1997 | Wyatt et al. | ................ 604/539 |
| 5,688,254 A | * | 11/1997 | Lopez et al. | ................ 604/535 |

(Continued)

FOREIGN PATENT DOCUMENTS

FR   2 642 139 A1 *   1/1989

(Continued)

*Primary Examiner*—James M. Hewitt
(74) *Attorney, Agent, or Firm*—Lahive & Cockfield, LLP; Anthony A. Laurentano, Esq.

(57) ABSTRACT

A medical connector adapted for placement between a catheter and a medical infusion or injection source includes a pair of interlocking half medical connector portions, one side of which attaches to the infusion source and the other side of which is coupled to the catheter connected to the patient and a locking mechanism for locking a medical connector portion to a medical fitting. The connection to the catheter and the infusion source can be via standard medical luer taper fittings, with or without specially designed locking mechanisms that prevent inadvertent disconnection. The medical connector itself is uniquely shaped and includes a raised surface feature and a recessed surface feature formed on the medical connector portions.

12 Claims, 9 Drawing Sheets

U.S. PATENT DOCUMENTS

| | | | | |
|---|---|---|---|---|
| 5,725,511 A | * | 3/1998 | Urrutia | 604/533 |
| 5,741,269 A | * | 4/1998 | McCredy | 606/106 |
| 5,925,028 A | * | 7/1999 | Delvigo | 604/404 |
| 5,947,937 A | * | 9/1999 | Urrutia et al. | 604/533 |
| 6,402,207 B1 | * | 6/2002 | Segal et al. | 285/330 |
| 6,422,607 B1 | * | 7/2002 | Kirby | 285/81 |
| 6,612,624 B1 | * | 9/2003 | Segal et al. | 285/330 |

FOREIGN PATENT DOCUMENTS

GB      771968    * 10/1955

* cited by examiner

FASTENING MECHANISM FOR MEDICAL CONNECTORS

RELATED APPLICATIONS

This application is a continuation of U.S. Pat. No. 6,612,624 filed on Apr. 17, 2002, which is a continuation-in-part of U.S. Pat. No. 6,402,207, filed Jun. 8, 1998, entitled "Safety Indexed Medical Connectors", the contents of which are herein incorporated by reference.

BACKGROUND OF THE INVENTION

The present invention relates to fluid connectors, and more particularly to fluid connectors used in medical environments and designed to ensure the correct and appropriate administration of medicaments to a patient.

Errors in prescribing and delivering medications to patients are, unfortunately, common in medical practice. Many of these mistakes result in patient injury or death, and even if the patient recovers fully, the cost to society of induced and prolonged hospital stays and greater patient charges are staggering. It is estimated that at least 25,000 incidents involving drugs administered to a patient by the wrong route occur annually, all of which are the result of preventable human error. The most common cause of confusion in route of administration is the universal nature of medical connectors and injection sites. Most medical connectors and infusion/injection sites are universal couplers that are designed to mate with and therefore accept most syringes and other fluid delivering devices. The most common types of infusion sites are rubber septa designed to be pierced by a needle, and female luer connectors designed to be connected to a syringe or medical tubing with a male luer fitting, either by friction fit or threaded lock. Both types of sites are commonly included in intravenous infusion tubing, on the ends of heparin locks, in stopcocks in all types of intravenous, arterial, epidural, and other type connectors, and even in devices not designed for medication or fluid infusion at all, such as esophageal stethoscopes and urinary catheters. The universal employment of rubber septum injection ports and female luer connectors is directly coupled to thousands of errors in which a medication or fluid designed to be given by one route has inadvertently been given by another route, sometimes with disastrous consequences.

Several additional problems arise from use of current technology. The use of needles for connecting infusion lines and the administration of medicines has led to many cases of needlestick injury and transmission of blood borne infections, including hepatitis and AIDS. The infusion of proper fluids through the needle and coupler is also prone to inadvertent failure due to unwanted disconnection of the needle from the rubber septum. Moreover, repeated piercing of the coupler with the needle can taint the sterile fluid pathway.

The prior art has attempted to address the foregoing concerns by employing needleless systems and locking connectors, but they too are designed as universal connectors which are subject to route of administration errors. For example, a patient may be connected to multiple fluid delivering devices, hence forming multiple fluid pathways. The medical connectors are typically coupled to fluid delivering and receiving devices by universal type connectors, such as luer fittings. Hence, an attending person may accidentally apply a medicament to the wrong fluid pathway since the universal connector accepts or can be coupled to conventional fluid delivering devices.

It is an object of this invention to develop a needleless, relatively safe, locking connector system that is fluid path-specific. That is, the system should allow only infusions or injections of the proper type to be connected to the specific catheter or tubing type. In order to maintain efficiency and ease of locating the proper connectors, especially in an emergency, the types of connectors should be easily determinable by inspection.

Other general and more specific objects of the invention will in part be obvious and will in part appear from the drawings and description which follow.

SUMMARY OF THE INVENTION

The invention described herein is designed to eliminate, prevent or reduce the occurrence of unwanted or accidental administration of fluids to the wrong fluid pathway through known universal connectors. The present invention addresses this problem by replacing the universal connector with unique specially configured male/female connector pairs, each coded for use with only one type of medical catheter or device (e.g., peripheral intravenous catheter, central venous catheter, arterial catheter, epidural catheter, dialysis catheter).

The present invention specifically describes in one aspect a family of medical connectors designed to attach a medical infusion or injection device to a patient catheter or device. It is comprised of pairs of male-female locking connectors. The mating surfaces are uniquely indexed so that only complementary halves of the appropriate set connect together. Preferably, the fluid path runs through the length of the connector halves, with complementary shape- and/or size-indexed pieces constructed coaxially with the fluid path in each half connector. When in use, the two halves are pressed together and via a number of possible techniques locked into position, thus completing the fluid path. The ends of the connector halves opposite the mating surfaces can attach to standard luer-type medical connectors, preferably female on one half and male on the other, in order to interpose the mated connector between a catheter or other patient receiving device and an infusion or fluid delivering device, such as an intravenous tubing set or a syringe. In certain specialized applications, female-female, or male-male outer ends can be incorporated; in still others, non-luer fittings may be incorporated, for example to facilitate piercing a vial or intravenous fluid container.

According to another aspect of the invention, one half of the connector can be permanently attached to a catheter, infusion tubing set or syringe. This facilitates use of the device in applications which are especially sensitive to errors in fluid or medication administration, to ensure correct drug administration in emergency situations. In another aspect, a valve can be incorporated into either or both halves of the connector pair which closes the fluid path when the two halves are not mated together, or may incorporate irreversible locking mechanisms to attach the connector half permanently to a catheter, tubing end or syringe.

The present invention also provides for a medical connector suitable for use in coupling a fluid delivering conduit to a fluid receiving conduit, such as a catheter adapted for insertion within a patient. The medical includes first and second connector housing parts having a first end sized to mate with the fluid receiving and delivering conduits and a second end having a selected first surface feature formed thereon. When assembled, the first surface feature of the first housing part couples with the second surface feature of the second housing part to form a fluid connection therebetween.

The present invention further provides a locking mechanism for locking the medical connector to a fluid conduit. The locking mechanism may include a ratchet mechanism that allows rotation of the medical connector about the fluid path in one direction only. As a result, once the medical connector has been attached to the fluid conduit, removal of the medical connector from the fluid conduit is difficult or impossible.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DESCRIPTION OF THE ILLUSTRATED EMBODIMENT

This present invention involves one or more, such as a family, of medical connectors with male and female halves which are shape- and/or size-indexed so that only complementary pairs of connectors may be coupled and then employed to deliver a fluid a patient along a selected fluid pathway. The connectors of the present invention help avoid accidental administration of a fluid to the wrong fluid pathway by ensuring that fluid delivering devices can only be connected to a fluid receiving device having a specific configuration. The present invention may be adapted to many different medical applications in the field of medical connectors, injection apparatus, and infusion devices.

Figure 1:
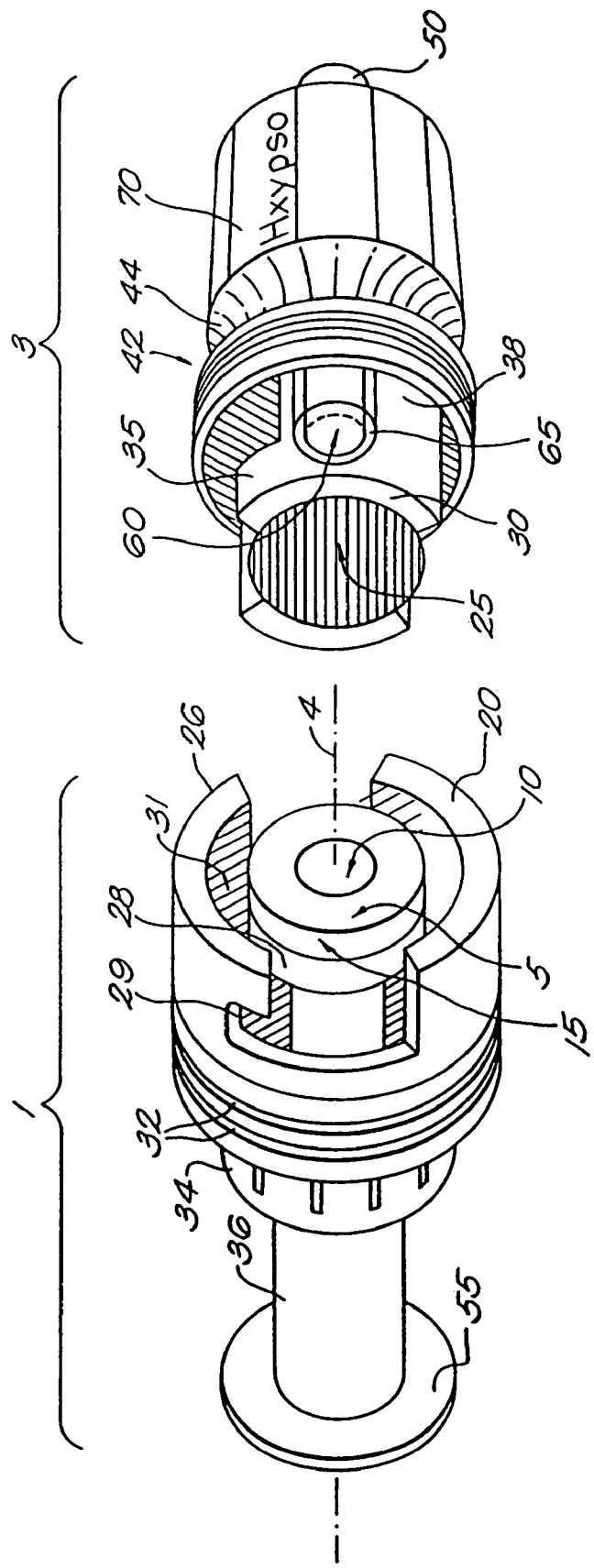
FIG. 1 is a perspective view of one embodiment of a medical connector incorporating a selectively configured connection mechanism employing both raised and recessed surface features according to the teachings of the present invention.
Figure 2:
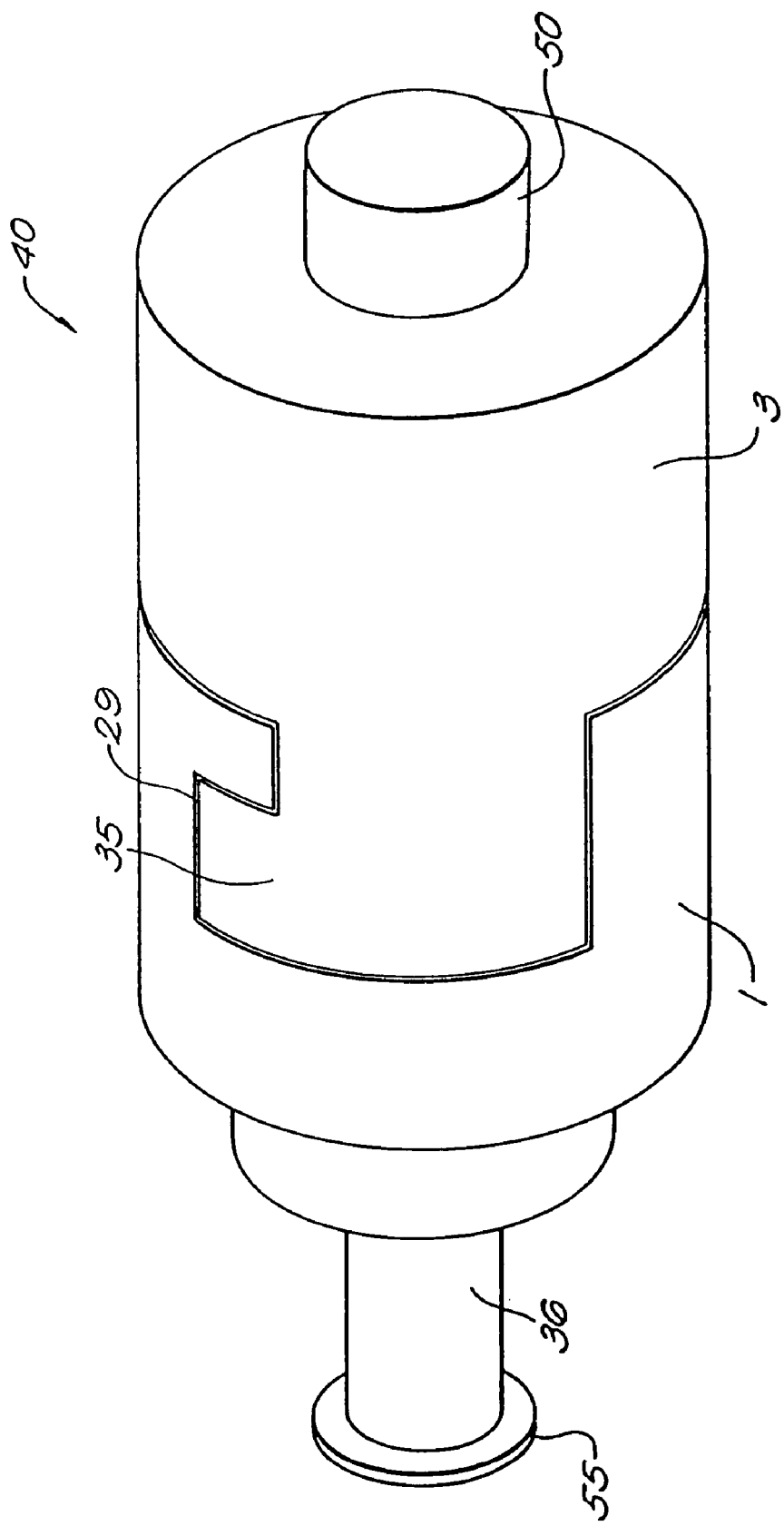
FIG. 2 is a perspective view of the medical connector of FIG. 1 disposed in a closed or assembled position.

FIG. 1 shows a perspective view of two general medical connector portions, designated as a first male medical connector portion 1 and a second female medical connector portion 3, which incorporate in their first ends, respectively, a protuberance 15 and a cavity 25 complementary in shape to the protuberance. These surface features allow the two connector halves to fit together in a fluid-tight seal, as shown in FIG. 2. A fluid path runs through the long axis 4 of the first portion 1 and the second portion 2. Specifically, the medical connector portion 1 includes a central fluid lumen 10 that extends longitudinally therethrough from one end to the other. Likewise, the other medical connector portion 3 includes a central fluid lumen 60 that passes longitudinally therethrough. When assembled, the fluid lumens 10, 60 are disposed in registration with one another to form an intermediate fluid pathway that connects a fluid delivering device to a fluid receiving device.

The illustrated first medical connector portion 1 has a surface feature formed on a mating end, such as the raised protuberance 15. The protuberance 15 can have many shapes, and as illustrated is an annulus having an outer, flattened surface 5 that is disposed generally perpendicular to the long axis 4 of the connector 1 and the lumen 10. The second medical connector 3 has a complementary shaped surface feature, such as recess or cavity 25, which seats the protuberance 15 of the first connector portion 1. The recess 25 ends in a floor stop 65 which is designed to stop the advance of the protuberance 15 when disposed within the recess. A Central lumen 60 forms a second fluid pathway within the connector 3 and extends substantially from the recessed first end to the opposite end.

The matable complementary shaped surface features 15,25 of the medical connectors are designed to be incompatible with conventional type fittings, such as luer taper fittings, which are a family of friction-fit, locking connectors of standardized size and shape, widely used in medical applications, and well known in the art. The surface features can have a variety of shape and sizes, such as illustrated in FIGS. 5A–5D.

The illustrated first medical connector 1 includes an outer housing having a recessed end which forms an outer annulus 26 that is coaxially disposed about the protuberance 15. The outer annulus 26 includes a number of channels 28 formed therein, which terminate in a lock or key portion 29, formed towards an intermediate portion of the medical connector. The medical connector 1 can further include a series of circumferential grooves 32 formed about the outer body portion of the connector. The grooves are preferably sized to seat a locking arm, FIG. 6C, that can be formed on the other medical connector part for locking or securing the two connector components together to form a fluid-tight seal.

With further reference to FIG. 1, the medical connector portion 1 further includes a stepped outwardly extending housing portion 34, and a further outwardly extending portion 36 that extends along the longitudinal axis 4. This portion terminates in a flange or collar 55 adapted to connect with a fluid receiving or delivering device. The other medical connector part 3 includes an outer housing portion 38 configured complementary to the mating end 20 of the other connector portion 1, so as to be able to couple thereto in a fluid sealing arrangement. Specifically, the outer housing portion 38 of the medical connector 3 terminates in a tab portion 35 that is designed to seat within the key portion 29 of the other medical connector portion 1. The connector 3 is further tapered at an intermediate portion 42 and includes a cut-out portion 44. The connector terminates in a chamfered end 70 having an axially extending connector 50.

Figure 6A:
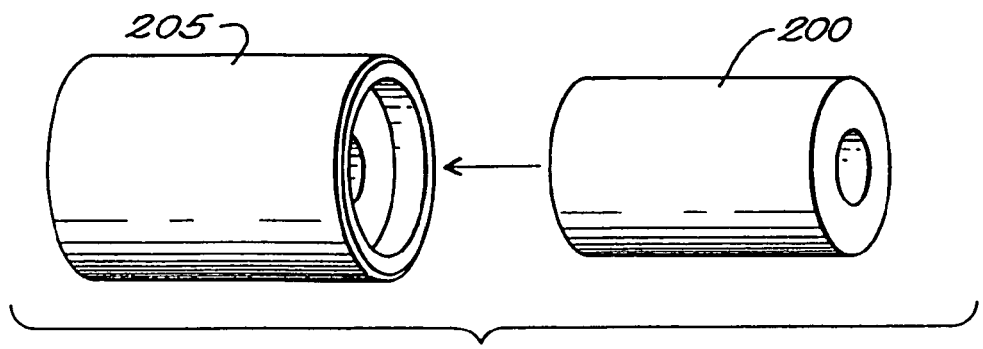
FIGS. 6A through 6C illustrate various constructions of a locking mechanism suitable for use with the medical connector of the present invention.
Figure 6B:
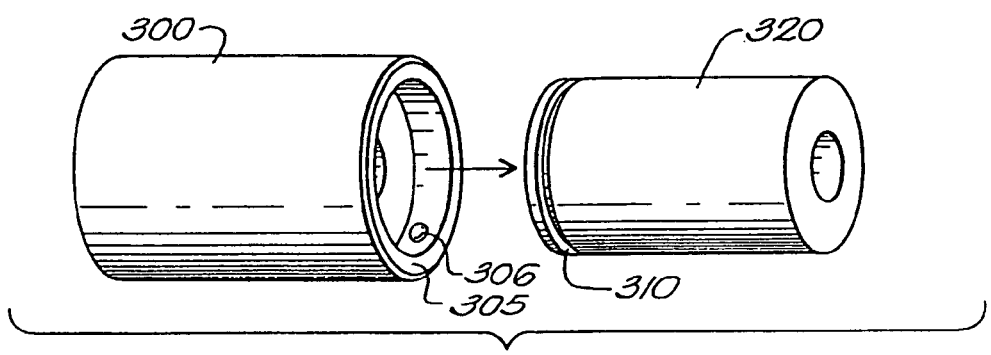
Figure 6C:
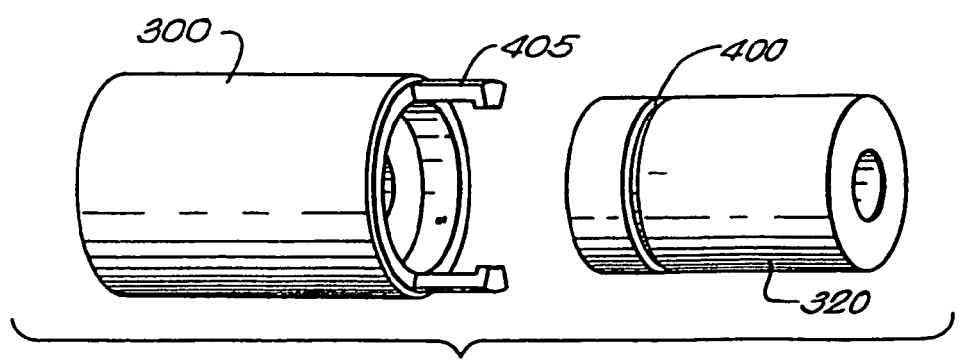

The two medical connector portions 1, 3 when mated together can either be held together by a friction fit arrangement, by the key locking scheme illustrated in FIG. 1, or by a number of other locking schemes, as shown in FIGS. 6A through 6C. The illustrated locking scheme involves seating the protuberance 15 in the recess 25 such that the mating portions of the two connectors are coaxially arranged. Furthermore, the outer housing 38 of connector 3 has an end 30 that seats within the space or channel 31 formed between the protuberance 15 and the outer annulus 26. Likewise, the outer end 20 of the protuberance is coaxially arranged with and seats about the outer surface or shell 38. In order to assemble the connector parts, the portions 1 and 3 are pressed together, and the outer housing portions rotated around its long axis so that the tab 35 engages and locks with the complementary key portion 29. The assembled medical connector portions form a secure, fluid-tight medical connector 40 that couple together various fluid devices, such as catheters, needles, or syringes connected to the luer fittings 55 and 50, as illustrated in FIG. 2.

The illustrated medical connector portions 1, 3 of the invention are designed to be application or path-specific. The male or first connector portion 1 of the medical connector 40 is configured to mate with only one type of mating surface, although selected others are also contemplated, and will not mate with other female type connectors. Thus a connector designated, for example, for epidural catheter injections is generally incapable of connection to a syringe intended for intravenous injection absent the specially configured surface feature. The identity of the connector type is readily recognizable by the skilled artisan from the shape or design of the mating surfaces, as well as from distinctive markings on the outer surfaces of the half connectors. These markings can include textured features, color coding and/or text labels, such as labels 70.

Each medical connector portion 1, 3 has an end 55, 50 opposite the mating surface or ends 20, 30 that are adapted to mate to a fluid delivering device, such as catheters, needles, syringes or other medical devices. In the illustrated connector of FIG. 1, the ends 55, 50 can be standard luer taper fittings, either slip or locking type, which are easily connected to the fluid delivering or receiving devices. Luer type fittings are well known and well characterized, and need not be described further herein. The use of safe and secure luer-type fluid fittings allow the safety medical connector 40 to be interposed between standard medical components now in widespread use. The medical connector 40 can also be permanently incorporated into various catheters, connectors, syringes, tubing sets, and other devices designed for patient connection, as shown in FIGS. 7A–7D.

Figure 3:
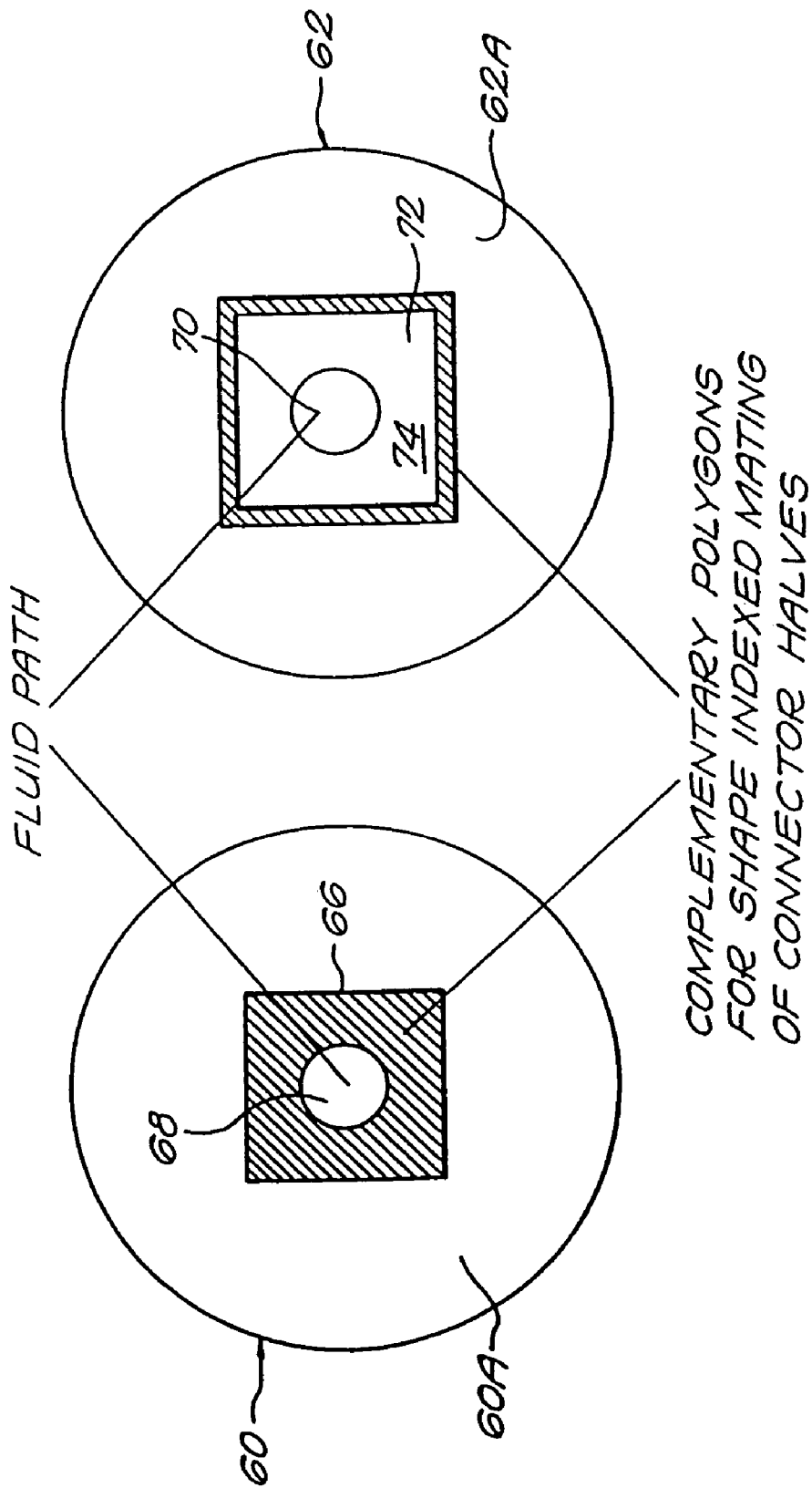
FIG. 3 is an end view of the two half portion of a medical connector illustrating another embodiment of the connection mechanism in accordance with the teachings of the present invention.
Figure 4:
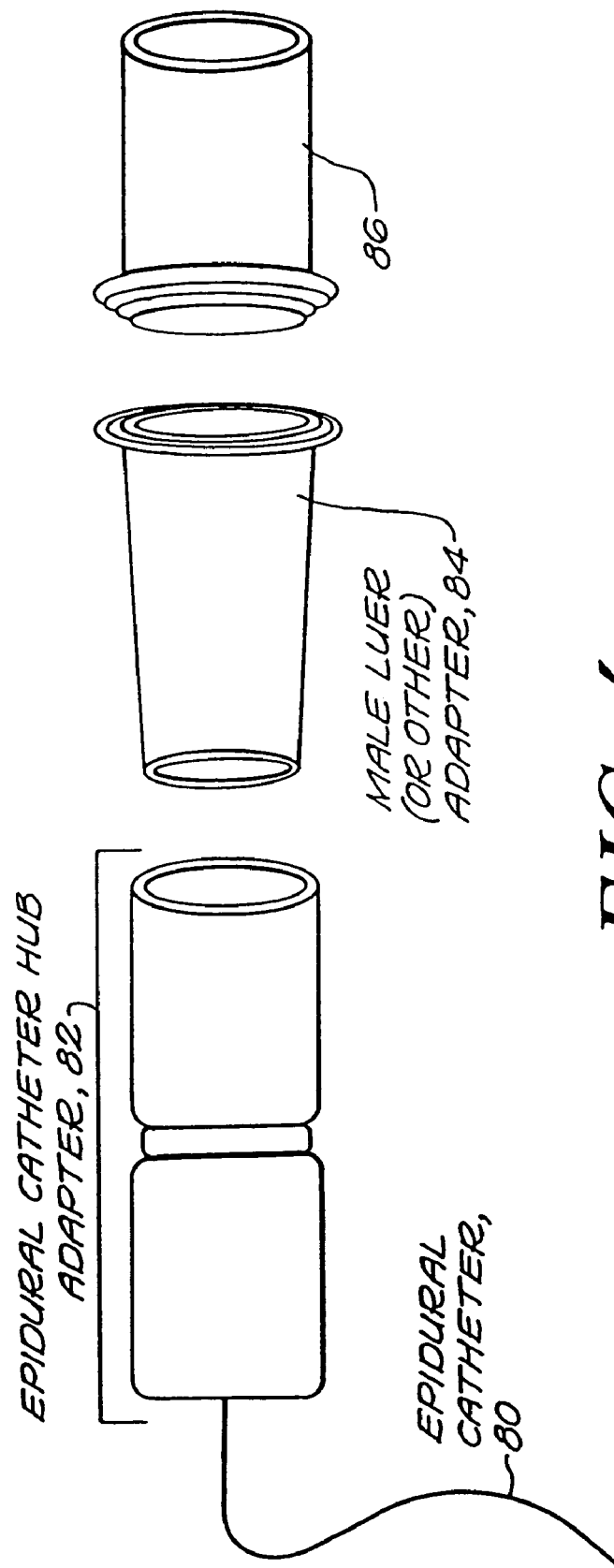
FIG. 4 is an unassembled perspective view of another embodiment of the medical connector in accordance with the teachings of the present invention.

FIG. 3 illustrates another type of connector design suitable for use in accordance with the present invention. The illustrated connector includes two connector portions 60, 62 designed to join together to form a fluid-tight seal for the injection or infusion of a medication or medical fluid, or alternatively for the evacuation of a body fluid, via a catheter or device placed into the patient's vein, artery, epidural or spinal space, or other body compartment. The medical connector portions 60 includes a quadrilateral shaped raised surface feature 66 extending from one end 60A. The connector includes a fluid lumen 68 formed therein that extends between the connector ends. The other connector portion 62 has a recessed surface feature 72 complementary in shape to the raised feature in order to accommodate and properly seat the raised feature to form a fluid tight seal. According to one practice, the end region 62A includes a cavity 72 that has a floor portion 74. The floor portion is apertured with an opening that defines the fluid lumen 70. The lumen extends between the connector ends.

When assembled, the protuberance 66 seats within the cavity 72 to dispose the lumen 68 in fluid communication with the lumen 70 to form a continuous fluid path along the assembled connector and between, for example, an infusion or injection source and a patient catheter. The two connector portions 60, 62 can be locked together using a variety of different schemes as discussed below. The locked pair of medical connector portions can include additional connection sites (such as luer fittings) on the ends opposite the mating surfaces 60A, 62A which allow the device to be inserted between the patient and the injection, infusion, or evacuation source. For example, the basic design can consist of standard luer taper fittings attached to each medical connector half. Therefore, an epidural catheter 80 can be connected via its female luer hub adapter 82 to a male luer fitting 84 coupled to one end of a medical connector, generally illustrated as medical connector portion 86, configured in accordance with the present invention. The connector 86 couples to the other connector half to complete the medical connection. According to one practice, the illustrated connector 86, when not coupled to its mating connector, generally cannot be connected to any standard syringe or medical tubing which is devoid of a complementary surface feature.

Figure 5A:
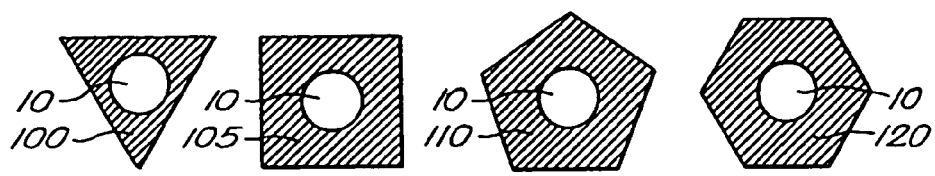
FIGS. 5A through 5D illustrate various constructions of the connection mechanism in accordance with the teachings of the present invention.

FIGS. 5A through 5D illustrate still other embodiments of the surface features which can be formed on the mating ends of the medical connectors in accordance with the present invention. In each case, a complementary pair of protuberances and recesses are incorporated into the medical connectors. In FIG. 5A, the protuberances can have a variety of geometric shapes, which are arranged coaxially around the lumen 10. The shapes of the surface features can further include a triangle 100, square 105, pentagon 110, hexagon 115, or other regular polygon or quadrilateral shape. As is readily apparent to those of ordinary skill, each illustrated surface feature can replace the cylindrical protuberance 15 of FIG. 1. The raised surface features fit into a complementary shaped and sized cavity formed in the other medical connector half.

Figure 5B:
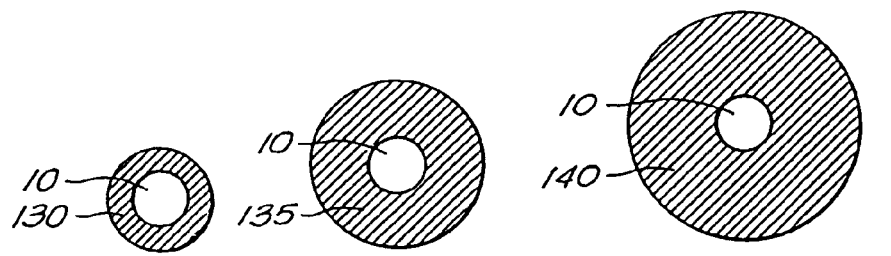
Figure 5C:
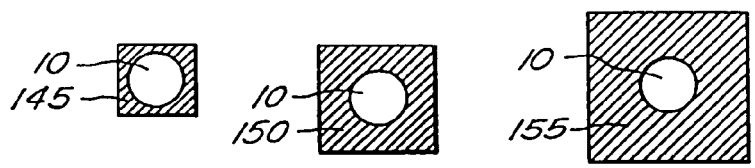
Figure 5D:
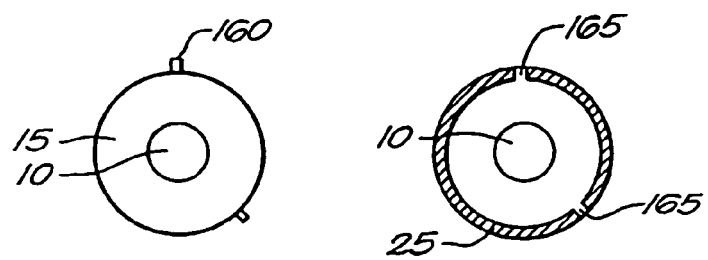

FIGS. 5B and 5C illustrate employing raised surface features that have varying sizes. In these instances, the lumen 10 is surrounded by a cylindrical protuberance of small 130, intermediate 135, or larger 140 diameter, or alternatively a regular polygon of small 145, intermediate 150, or larger 155 size. FIG. 5D illustrates employing radial projections in an outer surface of the connector half, to effectuate radial pin indexing. In this configuration, radially spaced pins 160 are arranged circumferentially about the protuberance 15. These pins uniquely mate with complementary slots 165 arranged radially within the walls of the cavity 25 formed in the other connector half.

The foregoing medical connectors can be fashioned from hard plastic or other suitably minimally deformable material, so that incompatible connector halves cannot mate in a fluid-tight manner. Attempts to do so will cause the fluid path to leak, preventing inadvertent injection. Integrity of the fluid path can be ensured either by a tight friction fit between the complementary connector parts, or by the inclusion of an integral rubber or other deformable gasket on the male portion of the connector pair. This gasket would be slightly larger in its non-deformed state than the complementary female half connector's cavity, so that when the two connectors are mated, the gasket deforms and causes a tight seal.

Two complementary medical connector portions can be joined together to form a complete medical connector. Once assembled, the connector portions can be locked into the mated or joined position in a variety of ways. Some examples of locking arrangements suitable for use with the medical connector of the present invention are illustrated in FIGS. 1 and 6A through 6C. As described above, the connector portions 1 and 3 of FIG. 1 include a key and tab engagement arrangement to secure the connector halves together. FIG. 6A illustrates a pair of medical connectors 200 and 205 which can be assembled and held together with a simple friction fit. In this configuration, the mating portion of connector 200 is slightly smaller in size than the complementary connector 205 so that when engaged, sufficient force is required to separate the connector pair such that ordinary injection pressures do not separate them. Specifically, the medical connectors 200, 205 require some amount of force to separate the connector portions. The tolerances of the two mating medical connector portions are such that the pressure in the fluid delivering or receiving conduits attached to the connector are generally insufficient to drive the pair apart.

FIG. 6B illustrates another of securing or locking the connectors 300 and 320 together. In this embodiment, the connector 300 includes a stepped axially extending lip portion 305 formed on the mating end of the connector. The lip of the larger connector includes a slightly raised portion or detent 306 extending radially inwardly towards or into the lumen. The lip 305 is adapted for engagement with a complementary channel or indent formed in the mating end of the other connector 320, which is of slightly smaller diameter. The two connector halves can lock together with a pushing action, with one side designed to pass over the other. When assembled, the smaller connector 320 is pushed within the larger connector half 300 until the lip 305 engages the complementary indent 310, thereby securing the connector portions together.

FIG. 6C shows the similar arrangement of two outer housings of slightly different diameters 300 and 320 with slots 400 formed on the outer surface of connector 320, which engage slightly spreadable or deformable fingers 405 attached to and extending from the other connector half.

Still other embodiments of securing mechanisms include providing connector portions that contain a central fluid lumen, and ending in luer or other fittings for connection to medical tubing, syringes, or catheters. The entire inner portion of the connector is adapted to spin freely around the axis of the fluid lumen. When assembling together the two medical connector halves, the inner portions of the connectors mate together, and then the outer housing portions of the connectors are twisted together to lock them. Several mechanisms for locking the outer portions are possible. The two outer housings could be designed with complementary deformable tabs and slots which engage when twisted together, threaded ends which screw together, or fingers on one part which lock into slots on the other part, as described above in connection with FIGS. 6A through 6C. Another embodiment of a securing mechanism can include configuring the inner mating portions of the connector portions so as not to spin along the axis of the fluid lumen.

As described above, the foregoing medical connectors function as a basic interface between standard fluid delivering and receiving devices, such as standard catheters and infection sources, via standard medical luer fittings. In the usual application, one connector portion of the present invention contains at its non-mating end a male luer fitting with or without a standard twist-lock feature, and the other connector contains a similarly positioned female luer fitting. In certain specialized applications, twin female or male luer adapters could be incorporated.

This medical connectors of the invention can also be fitted with connectors at the non-mating ends that allow its connection to other medical devices and containers. In one important embodiment of this invention, one connector half is permanently fused to or incorporated into a standard medical infusion device, so that use of a complementary connector is mandatory to access the catheter or device. For example, an epidural catheter adapter, which typically grips a 18 to 21 G epidural catheter and ends in a female luer fitting, is mounted to one end of the medical connector half. Only a syringe or tubing set incorporating or fitted with the complementary half connector can be used with this type of epidural catheter. Any catheter, injection adapter, tubing set, syringe, or device connecting to a patient catheter and currently using luer universal connectors can be adapted to incorporate half connectors of a given type from the present invention. The invention thus allows a family of safety injection sources and catheters to replace the inherently less safe universal connectors in wide use today.

The foregoing safety medical connectors are designed to be interposed between existing devices for medical infusions, injections, or aspirations. An additional feature of the present invention is the fusion of a half connector as illustrated in FIG. 1 into a standard medical connector or device. FIGS. 7A through 7D illustrate the incorporation of a safety connector half into an epidural catheter connector 500, which in turn is connected to an epidural catheter 505. Any of the mating and locking configurations of the present invention, for example the rectangular surface feature 510, can be incorporated into the end of the epidural catheter connector. The epidural catheter connector in turn mates with a complementary safety connector half 520. This connector half includes a complementary shaped surface feature that ensures that only medications intended for epidural delivery are injected through the epidural catheter, since only a specific surface feature 510 can mate with the connector half 520.

Figure 7A:
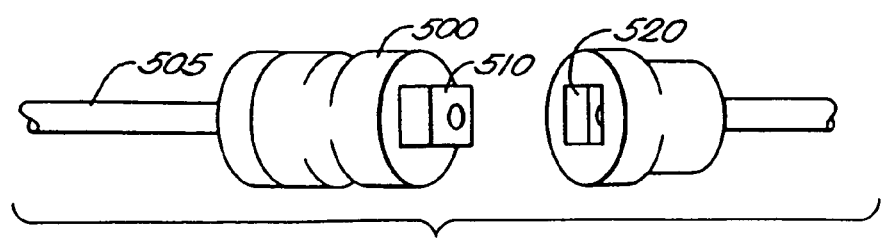
FIGS. 7A through 7D illustrate the manner in which the medical connector of the present invention can be coupled to various fluid delivering or receiving devices.
Figure 7B:
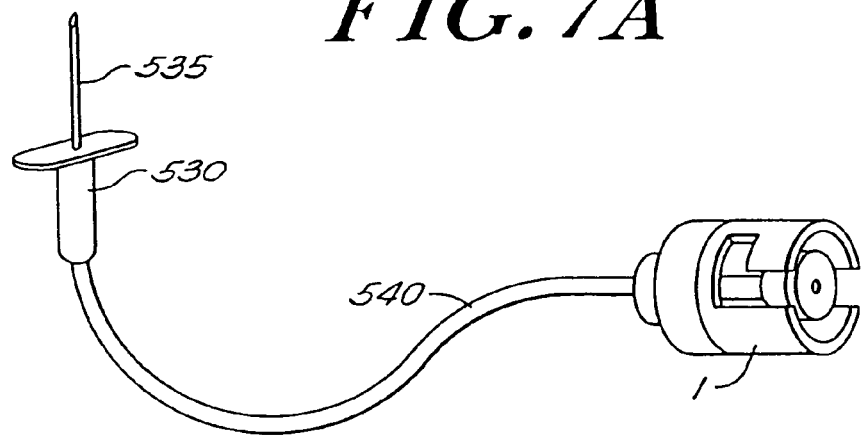
Figure 7C:
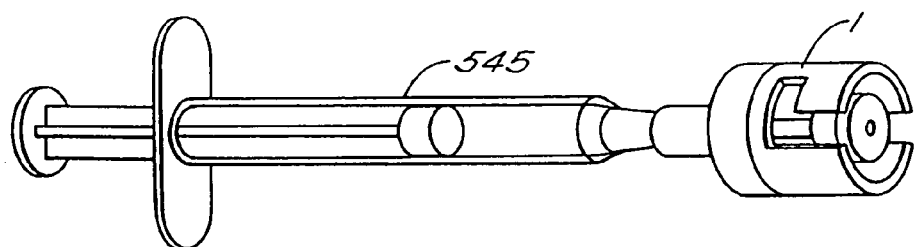
Figure 7D:
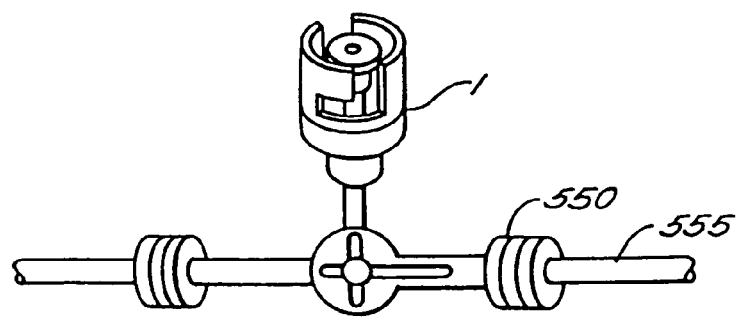

FIG. 7B illustrates another example of attachment mechanisms adapted for use with the medical connector of the present invention. The illustrated medical connector can be coupled to a hollow sharpened spike designed for piercing bags of intravenous fluids, blood products, or premixed intravenous medications; a connector to feeding tubes; or a connector for certain specialized catheters used in peritoneal dialysis. Specifically, a half connector 1 is incorporated into a tubing set for infusion of fluids or medications into a patient, typically comprised of tubing 540 and a spike 535 for piercing a container of fluid or medication, which can be seen to be infusing through a transparent drip chamber 530. In still another configuration, as shown in FIG. 7C, a half connector 1 is incorporated into a syringe 545. In another embodiment, as shown in FIG. 7D, a half connector 1 is incorporated into a three-way stopcock 550 which allows entry of medication or withdrawal of fluids or medications from a tubing set 555.

Other variations of the basic design of the medical connector of the present invention are contemplated by this invention and thus form part of the description. First, one medical connector half may be fused permanently or incorporated into an existing medical infusion or injection device. For example, a syringe prefilled with a medication that can only be given safely by a certain route could be fashioned with a half connector on its end. Only by mating with a catheter fitted with the appropriate complementary connector part (perhaps also permanently mounted) can the injection be given. Tubing sets designed for particular applications such as epidural anesthetic infusions can be fashioned with injection sites which only connect to other complementary connector parts. Thus, while allowing simple and needleless injection of additional medications, inadvertent injection of inappropriate medications would be significantly less likely, and hence prevented.

Figure 8A:
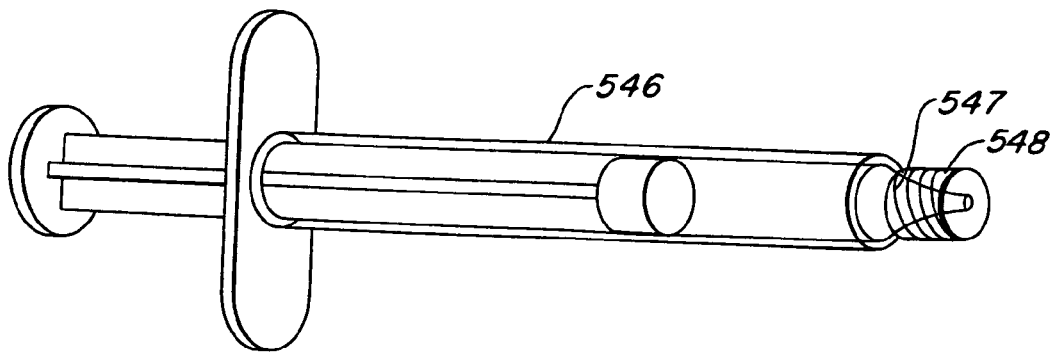
FIGS. 8A–8D illustrates the medical connector including a ratchet mechanism for locking the medical connector to a fluid conduit, illustrated as a syringe, according to one embodiment of the present invention.
Figure 8B:
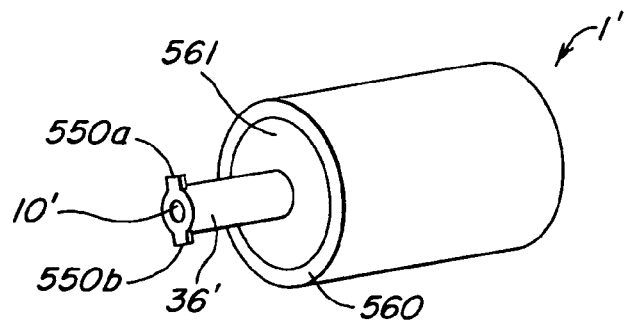

According to another embodiment, shown in FIGS. 8a–8d, the illustrative medical connector may include a ratchet mechanism to lock the medical connector to a fluid conduit. As shown in FIGS. 8a, a syringe 546 or other fluid delivering device includes a medical fitting 548 having screw threads 547 for receiving the medical connector 1'. As shown in FIG. 8b, the medical connector includes protrusions, such as teeth 550a and 550b, formed on the outwardly extending portion 36' that extends along the longitudinal axis. The teeth 550a, 550b screw into the threads 547 of the syringe 546 to couple the medical connector to the syringe 546.

Figure 8C:
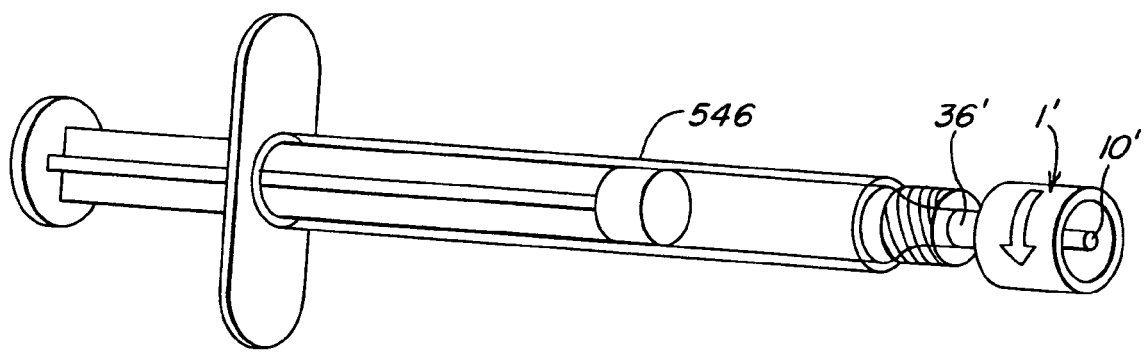

As shown in FIGS. 8b and 8c, the medical connector 1' includes an outer sleeve 560 and an inner body 561, which is integral with the outwardly extending portion 36' and includes the central fluid lumen 10' passing longitudinally therethrough. The outer sleeve 560 of the medical connector is adapted to spin about the inner body 561 in one direction only, illustrated by the arrow. The outer sleeve 560 include teeth on an inner surface that mesh with a pawl of the inner body 561 to prevent backward motion of the outer sleeve 560. One skilled in the art will recognize that any suitable mechanism for imparting, governing or preventing motion of the outer sleeve 560 relative to the inner body 561 in order to allow effective movement of the outer sleeve around the inner body in one direction only may be utilized.

Figure 8D:
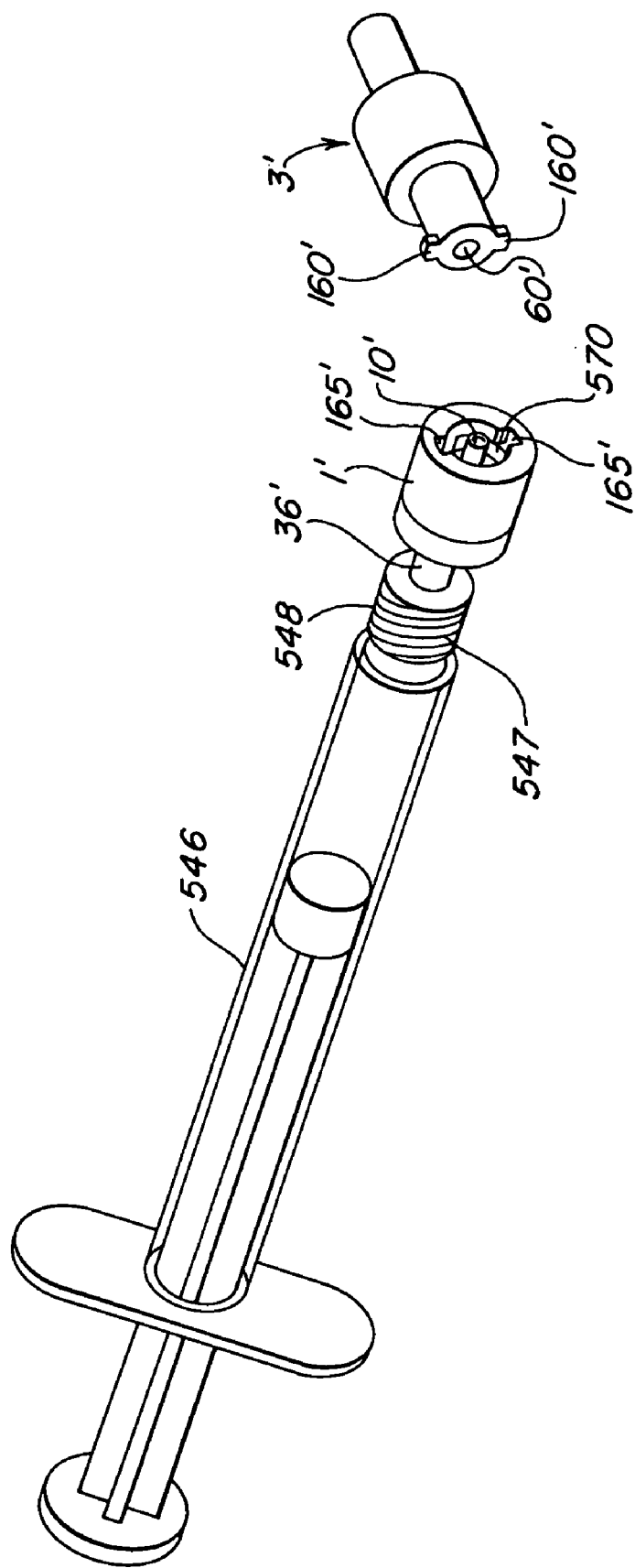

When the medical connector 1' is coupled to the syringe 546, as shown in FIGS. 8c and 8d, unscrewing of the medical connector from the syringe is difficult or impossible. The medical connector 1' is locked to the syringe 546 by inserting the outwardly extending portion 36' into the medical fitting 548 and rotating the medical connector in a second direction opposite the direction of the arrow. When the medical connector is rotated in the second direction, relative motion between the outer sleeve 560 and the inner body 561 is prevented by the ratchet mechanism and the outer sleeve 560 and the inner body 561 rotate together as one collective body. The teeth 550a, 550b of the medical connector 1' engage the threads 547 of the fitting and follow the ramped edge of the threads until the medical connector 1' is tightly secured to the syringe 546. However, when a user attempts to unscrew the medical connector 1' from the syringe 546 by rotating the medical connector about the longitudinal direction in the direction of the arrow (i.e. opposite the direction in which the medical connector was rotated to screw the medical connector to the syringe), the outer sleeve 560 rotates without turning inner body 561, extending portion 36' and teeth 550a, 550b. The teeth 550a, 550b remain lodged in the threads 547 of the fitting 548 and the medical connector 1' remains locked to the medical fitting 548. The relative movement of the outer sleeve 560 while the inner body 561 remains fixed thus prevents or impedes unscrewing of the medical connector from the syringe.

The illustrative medical connector 1' modifies the interface of the syringe 546, such that the syringe 546 can only mate with and form a fluid tight seal with a fluid conduit having a corresponding medical connector 3', shown in FIG. 8d, coupled thereto. According to the embodiment shown in FIGS. 8a through 8d, the first medical connector 1' includes slots 165' for receiving radially spaced pins 160' on the second medical connector 3'. The outer sleeve 561 includes internal threads 570 for receiving the pins 160' of the corresponding connector 3α. The central fluid lumen 10' of the first medical connector portion 1' extends longitudinally therethrough from one end to the other. Likewise, the complementary medical connector portion 3' includes a central fluid lumen 60' that passes longitudinally therethrough and is adapted to receive the protruding central fluid lumen 10' of the first connector portion 1'. To couple the medical connectors, the pins 160' are inserted into the complementary slots 165' and screwed into the threads 570, such that the first central fluid lumen 10' is inserted into the second central fluid lumen 60'. The assembled medical connector, comprising the first medical connector 1' and the second medical connector 3' thus forms a continuous fluid path that sealingly connects the syringe 546 and a fluid receiving device (not shown) that is connected to the second medical connector 3'.

In other designs, either or both medical connector portions can be fitted with a valve which is disposed in a normally closed position but is opened by appropriate mating with a complementary connector. A spring loaded mechanism closes the valve whenever the connector parts are disconnected, preventing fluid leaks and contamination of the lumen. The connector portions can also be configured to connect to standard medical infusion devices or catheters via essentially irreversible mechanisms so that, once connected, the safety of the device cannot be subverted by removing one half connector to restore a universal connection. An example of such an application is the preservation of one lumen of a central venous catheter exclusively for infusion of parenteral nutrition solutions. Commonly, warning labels or adhesive tape are placed over the rubber septum cap on the end of such a port, but these are easily subverted. A locked half connector from the present invention would all but eliminate this problem. Two such methods for locking the connectors are as follows. First, a modified screw-type male luer adapter with a wedge shaped enlargement incorporated into the screw threads may be substituted for an ordinary male luer adapter. A tab on the circumferential edge of a standard female luer adapter normally engages the threads in the male screw-type luer connector. When it meets the wedge in the threads of the modified adapter described here, it follows the ramped edge of the wedge, slightly deforming the threaded connector until it crosses the end of the wedge and returns to the threaded path. Because the wedge is placed so that the narrow end is contacted first during clockwise (tightening) rotation of the male luer adapter, unscrewing of the adapter once the wedge has been passed will be very difficult or impossible.

A second method for locking the present invention to an existing female luer adapter is to dispose a coaxial collar about the adapter. The inner male screw adapter is of standard design, and an outer collar is adapted to spin about its long axis (which includes the fluid path). Teeth arranged in the space between the male luer screw portion and the outer collar allow the outer collar to turn the inner male luer screw fitting only in the clockwise direction. Counterclockwise rotation is impossible because the teeth do not engage, and therefore once the modified male luer adapter has been screwed onto the female luer adapter, unscrewing them is difficult or impossible.

Still another modification of the connector of the invention is a family of accessory caps for covering the unmated half connectors of the basic device or its modifications as described elsewhere in this section. These caps have inner surfaces complementary to the male or female connector halves and insert over the mating surface of the connector half, preferably with a friction-fit.

This invention is designed to be used in both routine and emergency medical care. As such, simple and rapid identification of the complementary half connectors is important. Besides inspection of the mating surfaces themselves, a variety of techniques may be utilized to ease identification of the connectors (see Section 5). The preferred implementation of this technology into medical practice would involve standardization of the various connector types to be used only for certain catheters. For example, there could be one type only used for epidural catheters, one for peripheral intravenous catheters, and another for central venous catheters.

In certain applications, the medical connectors of the present invention may be advantageously employed with indwelling lines, i.e., central and peripheral intravenous lines, to offer selectivity relative to the fluid delivering device. For example, a syringe filled with a medicament that can be safely administered both peripherally and centrally, such as morphine, should be able to mate, via the medical connectors of the present invention, with the central and peripheral intravenous lines. In this embodiment, a pair of first housing parts having the same surface feature are coupled to both fluid receiving or indwelling pathways. The syringe (fluid delivering device) has coupled thereto a connector half that has a shape complementary to the shape of the other surface feature, thus enabling this connector and syringe to couple to both fluid pathways, and nothing else, if desired. However, a medicament that is not safely administered peripherally, such as potassium chloride, can be pre-filled in a syringe that could mate only with the connector half associated with the central line. Hence, the central intravenous line or pathway mates with both the central and peripheral compatible syringes, but the peripheral line connector only mates with the peripheral syringe. The central and peripheral lines can be manufactured with such fittings as integral parts, or as irreversibly attachable connectors when site specificity is warranted.

The general concept embodied in this technology, in summary, is that medical connectors are made path-specific rather than universal. This general description is of a pair of connectors disposed between standard fluid delivering and receiving devices.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A medical connector suitable for use in coupling a fluid delivering conduit to a fluid receiving conduit for administering fluid to a patient, said medical connector comprising:
  a first medical connector housing part having a first end sized to mate with a first medical fitting on one of said fluid receiving conduit and said fluid delivering conduit and a second end having a selected first surface feature formed thereon,
  second medical connector housing part having a first end configured to mate with a second medical fitting on one of said fluid receiving conduit and said fluid delivering conduit, and a second end having a selected second surface feature complementary in shape to the first surface feature of the first housing part, so that when assembled the first surface feature of the first housing part couples with the second surface feature of the second housing part to form a fluid connection therebetween, and
  a locking mechanism for locking together said first medical connector housing part and said first medical fitting, comprising a protrusion on the first end of the first medical housing part and screw threads on said first medical fitting adapted to receive the protrusion,
  wherein said first surface feature is sized and configured so as to only mate with the complementary shaped second surface feature to prevent another fluid delivering conduit associated with a differently configured surface feature from being connected to the fluid receiving conduit, thereby preventing the accidental administration of another fluid to the patient through the first and second housing parts.

2. The medical connector of claim 1, wherein the first medical connector housing part comprises:
  an inner body rigidly connected to the protrusion and containing a central fluid lumen; and
  an outer sleeve surrounding the inner body configured to rotate in a first direction about the inner body.

3. The medical connector of claim 2, wherein the first medical connector housing part further includes a ratchet mechanism to prevent rotation of the outer sleeve in a second direction opposite the first direction.

4. The medical connector of claim 3, wherein the ratchet mechanism comprises teeth on an inner surface of the outer sleeve engaging a pawl formed on an outer surface of the inner body.

5. The medical connector of claim 3, wherein the first medical connector housing part is locked to the first medical fitting by inserting the protrusion into the threads and rotating the medical connector in the second direction such that the protrusion engages the threads, thereby screwing the first medical connector housing part into the first medical fitting.

6. The medical connector of claim 5, wherein rotation of the medical connector in the first direction causes the outer sleeve to rotate about the inner body while the protrusion is maintained in an engaged position with the threads.

7. A method of administering fluid to a patient, comprising
  providing a fluid receiving conduit connected to the patient and having a first medical fitting coupled to a distal end of the fluid receiving conduit, said first medical fitting including screw threads;
  locking a first medical connector housing part to said first medical fitting, wherein said first medical connector housing part has a first end having a protrusion adapted to mate with the screw threads of the first medical fitting, and a second end having a selected first surface feature formed thereon,
  providing a fluid delivering conduit associated with a fluid source and having a second medical fitting coupled to a distal end of the fluid delivering conduit,
  attaching a second medical connector housing part to said second medical fitting, wherein said second medical connector housing part has a first end adapted to mate with the second medical fitting, a second end having a selected second surface feature complementary in shape to the first surface feature of the first housing part, and connecting said first medical connector housing part to said second medical connector housing part so that when assembled the first surface feature of the first housing part couples with the second surface feature of the second housing part to form a dedicated fluid path from the fluid source to the patient, wherein said first surface feature is sized and configured so as to only mate with the complementary shaped second surface feature to prevent another fluid delivering conduit associated with a differently configured surface feature from being connected to the fluid receiving conduit and wherein one of the first and second medical connector housing parts includes a set of valves to prevent fluid flow through the dedicated fluid path unless the first housing part is properly mated with the second housing part, thereby preventing the accidental administration of another fluid to the patient through the first and second housing parts.

8. The method of claim 7, wherein the first medical connector housing part comprises:

an inner body rigidly connected to the protrusion and containing a central fluid lumen; and an outer sleeve surrounding the inner body and configured to rotate in a first direction about the inner body.

9. The method of claim 8, wherein the first medical connector housing part further includes a ratchet mechanism to prevent rotation of the outer sleeve in a second direction opposite the first direction.

10. The method of claim 9, wherein the ratchet mechanism comprises teeth on an inner surface of the outer sleeve engaging a pawl formed on an outer surface of the inner body.

11. The method of claim 9, wherein the first medical connector housing part is locked to the first medical fitting by inserting the protrusion into the threads and rotating the medical connector in the second direction such that the protrusion engages the thread, thereby screwing the first medical connector housing part into the first medical fitting.

12. The method of claim 11, wherein rotation of the medical connector in the first direction causes the outer sleeve to rotate about the inner body while the protrusion is maintained in an engaged position with the threads.

* * * * *